(12) United States Patent
Jaffari et al.

(10) Patent No.: US 11,488,720 B2
(45) Date of Patent: Nov. 1, 2022

(54) THERMAL STRESS RISK ASSESSMENT USING BODY WORN SENSORS

(71) Applicant: LifeBooster Inc., Vancouver (CA)

(72) Inventors: Sam Jaffari, Vancouver (CA); Lawrence Chee, Vancouver (CA); Dan Robinson, Vancouver (CA)

(73) Assignee: LifeBooster Inc., Vancouver (CA)

( * ) Notice: Subject to any disclaimer, the term of this patent is extended or adjusted under 35 U.S.C. 154(b) by 421 days.

(21) Appl. No.: 16/809,305

(22) Filed: Mar. 4, 2020

(65) Prior Publication Data

US 2020/0286624 A1 Sep. 10, 2020

Related U.S. Application Data

(60) Provisional application No. 62/813,595, filed on Mar. 4, 2019.

(51) Int. Cl.
| | |
|---|---|
| *G16H 50/30* | (2018.01) |
| *G01S 19/01* | (2010.01) |
| *G01D 21/02* | (2006.01) |
| *A61B 5/0205* | (2006.01) |
| *G16H 40/67* | (2018.01) |
| *G01K 13/20* | (2021.01) |
| *A61B 5/11* | (2006.01) |
| *A61B 5/024* | (2006.01) |
| *A61B 5/0533* | (2021.01) |
| *A61B 5/389* | (2021.01) |

(52) U.S. Cl.
CPC ......... *G16H 50/30* (2018.01); *A61B 5/02055* (2013.01); *G01D 21/02* (2013.01); *G01K 13/20* (2021.01); *G01S 19/01* (2013.01); *G16H 40/67* (2018.01); *A61B 5/02438* (2013.01); *A61B 5/0533* (2013.01); *A61B 5/1112* (2013.01); *A61B 5/1114* (2013.01); *A61B 5/1123* (2013.01); *A61B 5/389* (2021.01); *A61B 2560/0252* (2013.01); *A61B 2560/0257* (2013.01); *A61B 2562/029* (2013.01)

(58) Field of Classification Search
None
See application file for complete search history.

(56) References Cited

U.S. PATENT DOCUMENTS

2007/0063850 A1\* 3/2007 Devaul ................ A61B 5/0024
340/573.1

FOREIGN PATENT DOCUMENTS

WO WO-2017109919 A1 \* 6/2017

\* cited by examiner

*Primary Examiner* — Kristy A Haupt
(74) *Attorney, Agent, or Firm* — Dergosits & Noah LLP; Todd A. Noah

(57) ABSTRACT

Methods, systems and computer program products provide for a Risk Assessment Engine that receives body ambient temperature data captured by a sensor in contact with a person. The Risk Assessment Engine characterizes types of activities performed by the person during a time range associated with the body ambient temperature data. The Risk Assessment Engine determines a risk classification individualized for the person based on respective workloads and the corresponding allocations of work and rest experienced by the person during performance of the characterized types of activities.

20 Claims, 6 Drawing Sheets

THERMAL STRESS RISK ASSESSMENT USING BODY WORN SENSORS

CROSS-REFERENCE TO RELATED APPLICATIONS

This application claims the benefit of U.S. Provisional Patent Application No. 62/813,595, filed Mar. 4, 2019, which is hereby incorporated by reference in its entirety.

TECHNICAL FIELD

The present disclosure relates generally to receiving sensor data and more specifically to identifying risks based on the sensor data.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

In conventional systems, wet bulb globe temperature ("Wbgt") devices are normally handheld devices that do not lend themselves to being worn on the body. Wbgt devices provide a quantified metric that captures all the parameters that impact the body's ability to maintain a safe core body temperature through evaporation. Key parameters that impact heat stress include temperature, humidity, pressure and radiant energy.

SUMMARY

Embodiments disclosed herein define a body ambient temperature measurement as a quantitative metric of temperature in close proximity to the skin obtained via one or more body worn sensors. The body ambient temperature replaces the Wbgt in its application to temperature standards that indicate, for example, that a climatized individual performing a job with a 60% allocation of work with a heavy workload, must not exceed a Wbgt of 27.5 degrees Celsius to remain safe and not be thermally at risk. The body ambient temperature accounts for temperature, humidity, pressure, and radiant energy. Unlike the Wbgt, body ambient temperature provides an advantage of not requiring a clothing adjustment factor.

A body sensor may be worn underneath, for example, the outermost layer of clothing to capturing a person's body ambient temperature. To provide a better representation of the skin temperature across the entire upper body, an array of body sensors could be worn on the upper body. A weighted average across the readings of all the worn sensors may thereby performed to calculate body ambient temperature value at any given time.

The disclosed embodiments herein are generally directed to a Risk Assessment Engine. A risk assessment represents a thermal stress risk at a given time—or period of time—during which a person performs various types of activities. The risk assessment is based on the type of activities performed by the person which are represented, in part, by raw data captured by a sensor(s) worn by the person. The Risk Assessment Engine characterizes the person's activities according to pre-defined activities. The pre-defined activities are associated with a workload category, such as light, medium/moderate, heavy and very heavy.

In addition, the Risk Assessment Engine determines the person's allocation of work, which represents a percentage of time within a time period (such as an hour) that the person is engaged in activities of a certain type(s) of workload or at rest. Body ambient temperature captured by the sensor(s) expectedly increases when a person's work allocation of activities favors more activities over rest and/or the person is performing activities with heavy to very heavy workloads—as opposed to medium to light workloads.

Safety threshold temperatures are predetermined for activities of various workload categories with respect to various allocation of work ranges, such as allocation of work range 0%-25% and 26%-50%, where 50% indicates that a person engages in activities as often as the person rests. An allocation of work at 100% represents a person who has no rest, and such an 100% allocation of work would certainly be corelated with an increase in body ambient temperature. The higher one's body ambient temperature increases with respect to an allocation of work that includes certain types of heavy to very heavy workloads, the predetermined safety threshold temperature necessary to avoid thermal stress risk inevitably decreases. In contrast, as one's body ambient temperature decreases with respect to a more restful allocation of work that includes certain types of activities that carry lighter workloads, the predetermined safety threshold temperatures necessary to avoid thermal stress risk inevitably increases. In other words, a more rested person engaged in lighter workloads is less likely to be exposed to a risk of thermal stress until their body ambient temperature exceeds a higher predetermined safety threshold temperature. However, if that person was engaged in the lighter workloads in an environment that included very warm outdoor temperatures, then that person's body ambient temperature may still pass the higher predetermined safety threshold temperature regardless of their lighter workload and restful allocation of work.

The Risk Assessment Engine automatically and continuously quantifies thermal risk assessments based on direct sensor measurements of a person's body dynamics and surrounding environment. A sensor(s) worn by a person performs continuous data capture and the captured raw data (body ambient temperature data) may be sent to a cloud computing infrastructure that hosts the Risk Assessment Engine. Upon receipt by the cloud computing infrastructure, the Risk Assessment Engine performs a sequence of data trimming, data synchronization, data transformation and pattern recognition techniques to identify one or more pre-defined activities indicated in part by the captured raw data (body ambient temperature data).

The Risk Assessment Engine obtains a workload of each pre-defined activity identified in the captured raw data (body ambient temperature data). In one embodiment, the workload may be defined by a metabolic rate in units of watts that is experienced during performance of a pre-defined activity identified in the captured raw data. In addition, an allocation of work during a time range during which the identified pre-defined activity was performed is additional determined. In one embodiment, the allocation of work may be a ratio of work time and rest time that occurred when the person performed the identified pre-defined activity. Given the workload and the allocation of work experienced by person while performing the identified pre-defined activity, the Risk Assessment Engine determines a risk classification representing the person's degree of thermal risk exposure. It is understood that risk classification for any number of persons performing one or more pre-defined activities can be graphically represented in a graphical user interface dashboard associated with Risk Assessment Engine.

The disclosed embodiments generally include a method and computer program product for the Risk Assessment Engine. The Risk Assessment Engine receives body ambient temperature data captured by a sensor in contact with a person. The Risk Assessment Engine characterizes types of activities performed by the person during a time range associated with the body ambient temperature data. The Risk Assessment Engine determines a risk classification (such as a thermal risk classification) individualized for the person based on respective workloads and the corresponding allocations of work and rest experienced by the person during performance of the characterized types of activities.

The disclosed embodiments may also include a system for a Risk Assessment Engine. The system may include one or more processors; and a non-transitory computer readable medium storing a plurality of instructions, which when executed, cause the one or more processors to: receive body ambient temperature data captured by a sensor in contact with a person, characterize types of activities performed by the person during a time range associated with the body ambient temperature data and determine a risk classification individualized for the person based on respective workloads and the corresponding allocations of work and rest experienced by the person during performance of the characterized types of activities.

BRIEF DESCRIPTION OF THE DRAWINGS

In the following drawings like reference numbers are used to refer to like elements. Although the following figures depict various examples, the one or more implementations are not limited to the examples depicted in the figures.

DETAILED DESCRIPTION

In accordance with embodiments described herein, there are provided methods, systems and computer program products for a Risk Assessment Engine that determines a risk classification individualized for a person(s) based on the types of activities the person(s) performs while wearing a sensor(s).

Any of the embodiments described herein may be used alone or together with one another in any combination. The one or more implementations encompassed within this specification may also include embodiments that are only partially mentioned or alluded to or are not mentioned or alluded to at all in the abstract. Although various embodiments may have been motivated by various deficiencies with the prior art, which may be discussed or alluded to in one or more places in the specification, the embodiments do not necessarily address any of these deficiencies. In other words, different embodiments may address different deficiencies that may be discussed in the specification. Some embodiments may only partially address some deficiencies or just one deficiency that may be discussed in the specification, and some embodiments may not address any of these deficiencies.

Some embodiments described herein may be described in the general context of computing system executable instructions, such as program modules, being executed by a computer. Generally, program modules include routines, programs, objects, components, data structures, etc. that performs particular tasks or implement particular abstract data types. Those skilled in the art can implement the description and/or figures herein as computer-executable instructions, which can be embodied on any form of computing machine program product discussed below.

Some embodiments may also be practiced in distributed computing environments where tasks are performed by remote processing devices that are linked through a communications network. In a distributed computing environment, program modules may be located in both local and remote computer storage media including memory storage devices.

Figure 1:
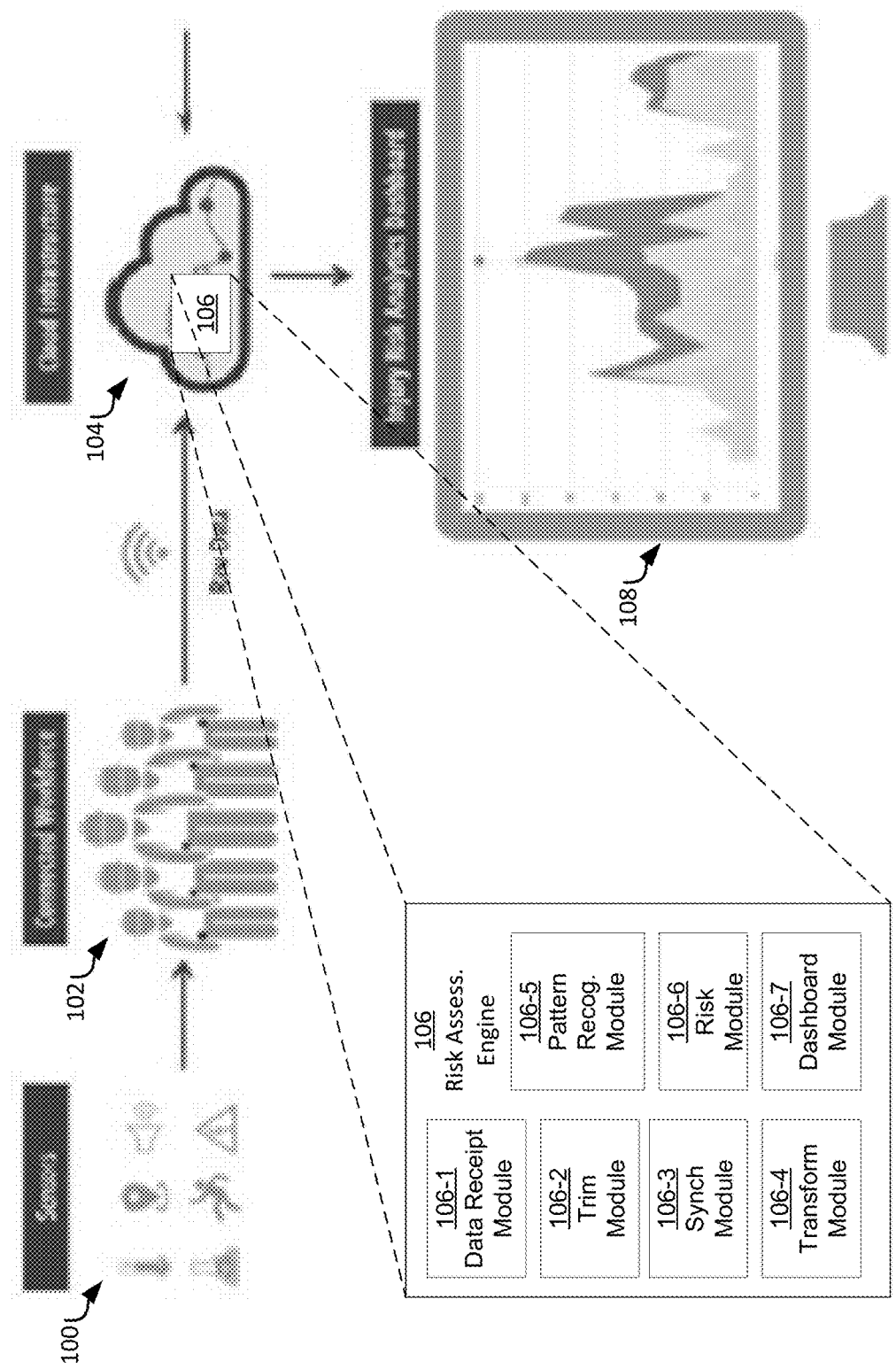
FIG. 1 is a high-level diagram of an environment for determining a risk assessment, in an embodiment.

As shown in FIG. 1, a plurality of employees 102 each wear one or more sensors 100 to form a connected workforce. The sensors continuously measure each employee's body ambient temperature as well as motion data representative of their various activities during a work shift. The sensors may also detect conditions surrounding each employee, such as outdoor and indoor temperature. The raw data captured by each sensor worn by the respective employees is continuously uploaded to a Risk Assessment Engine 106 that is hosted within a cloud computing infrastructure 104. The Risk Assessment Engine 106 outputs data to a risk analytics dashboard 108, which provides various graphs and data tables representing data characteristics related to each employee's thermal stress risk. For example, each employee may be associated with their own dashboard and an enterprise-wide analytics dashboard system 108 provides access to each employee-dedicated dashboard.

The Risk Assessment Engine 106 includes a plurality of modules for execution of the operations, steps, methods, actions and calculations described herein. The modules may include computer hardware and software instructions provided in a non-transitory executable medium. The Risk Assessment Engine 106 includes a data receipt module 106-1 for receiving raw data captured from a plurality of sensors 100 associated with a plurality of peoples, such as multiple employees 102 of a connected workforce. The Risk Assessment Engine 106 includes a trim module 106-2 for trimming the raw data from the sensors and external data from external data sources. In various embodiments, data may be trimmed in order to discard data associated with timestamps that occur outside of a relevant time period, such as a relevant work shift of an employee. The Risk Assessment Engine 106 includes a synchronization module 106-3 that pairs trimmed raw data and trimmed external data based on matching timestamp data. The Risk Assessment Engine 106 includes a transformation module 106-4 that increases data accuracy, reduce data errors and perform data conversions.

The Risk Assessment Engine 106 includes a pattern recognition module 106-5 that identifies characteristics in transformed data that indicates the employee engaged in (or is engaging in) an activity that is similar to a pre-defined activity. By characterizing a portion of the employee's transformed data as an appropriate pre-defined activity, the Risk Assessment Engine 106 can model the employee's workload and allocation of work. The Risk Assessment Engine 106 includes a risk module 106-6 that determines a risk assessment based in part on the employee's workload, allocation of work and body ambient temperature data captured by one or more sensors. The Risk Assessment Engine 106 includes a dashboard module 106-7 that generates graphical rendering data based on the employee's workload, allocation of work and body ambient temperature data.

Figure 2:
FIG. 2 is a high-level diagram of an exemplary graphical user interface dashboard, in an embodiment.

As shown in FIG. 2, a graphical user interface dashboard 200 for a Risk Assessment Engine 106 is illustrated. The dashboard 200 may be associated with body ambient temperature data captured by a sensor(s) in contact with an employee. The dashboard 200 includes a workload statistics table 202. The workload statistics table 202 provides a list of workload categories (rest, light, medium, heavy, very heavy) and a percentage of time the employee has engaged in work tasks that are categorized according to the workload categories. The dashboard 200 includes a risky events graph 202. The risky events graph 204 displays one or more lines of color contrast 206 to represent a reference time(s) at which the body ambient temperature data of the employee is above a threshold temperature for the type of activity performed by the employee at the same reference time.

Pre-determined threshold temperature values may be defined for each workload category (light, medium/moderate, heavy, very heavy) within a percentage range of allocation of work. If the allocation of work is between 50%-75%, then there will be threshold temperature values for each workload category. If the allocation of work is between 0%-25%, then there will be other threshold temperature values for each workload category. For example, if a person's allocation of work is between 50%-75% and that person is performing a first characterized type of activity that results in a medium/moderate workload, a first threshold temperature value may be 29 degrees. However, if the person's allocation of work is between 0%-25% and that person is performing a second characterized type of activity that also results in a medium/moderate workload, a second threshold temperature value may be 31.5 degrees. As shown by the exemplary first and second threshold temperature values, a person experiencing a lower extent of allocation of work between 0%-25% will not incur a thermal stress risk until the employee's body ambient temperature data goes above 31.5 degree. However, a higher range of workload allocation (50%-75%) inevitably results in a thermal stress risk at a lower 29 degrees. Therefore, the risky events graph 204 will present one or more lines of color contrast 206 when an employee's body ambient temperature data is above the threshold temperature value that is appropriate for the employee's allocation of work percentage and workload category for the type of activity the employee performed.

The dashboard 200 includes a temperature graph 208 which graphs the employee's body ambient temperature 210 and threshold temperature 212 as a function of time. The temperature graph 208 may also include a cursor 214 that highlights a comparison of an employee's body ambient temperature to the appropriate threshold temperature at a particular point in time.

Graph portion 216 represents a point of time at which an employee's work shift begins, which results in fast increase in body ambient temperature. Graph portion 218 represents a drop in the employee's body ambient temperature as the employee's workload decreases. Therefore, the threshold temperature rapidly increases because as the employee's work allocation decreases, the employee can afford to experience a higher body ambient temperature before being put at risk of thermal exposure. Graph portion 220 shows climbing ambient body temperature even though the work allocation stays at a lower percentage. This indicates that the employee's body ambient temperature has increased due to sun exposure and not as a result of the strain of the employee's workload. Graph portion 222 shows that the threshold temperature remains relatively low and constant as both the allocation of work and workload remain high while the employee is still performing activities outdoors. It is understood that in various embodiments, the table 202 and graphs 204, 208 are rendered in real-time as the employee is engaged in one or more tasks and activities.

Figure 3:
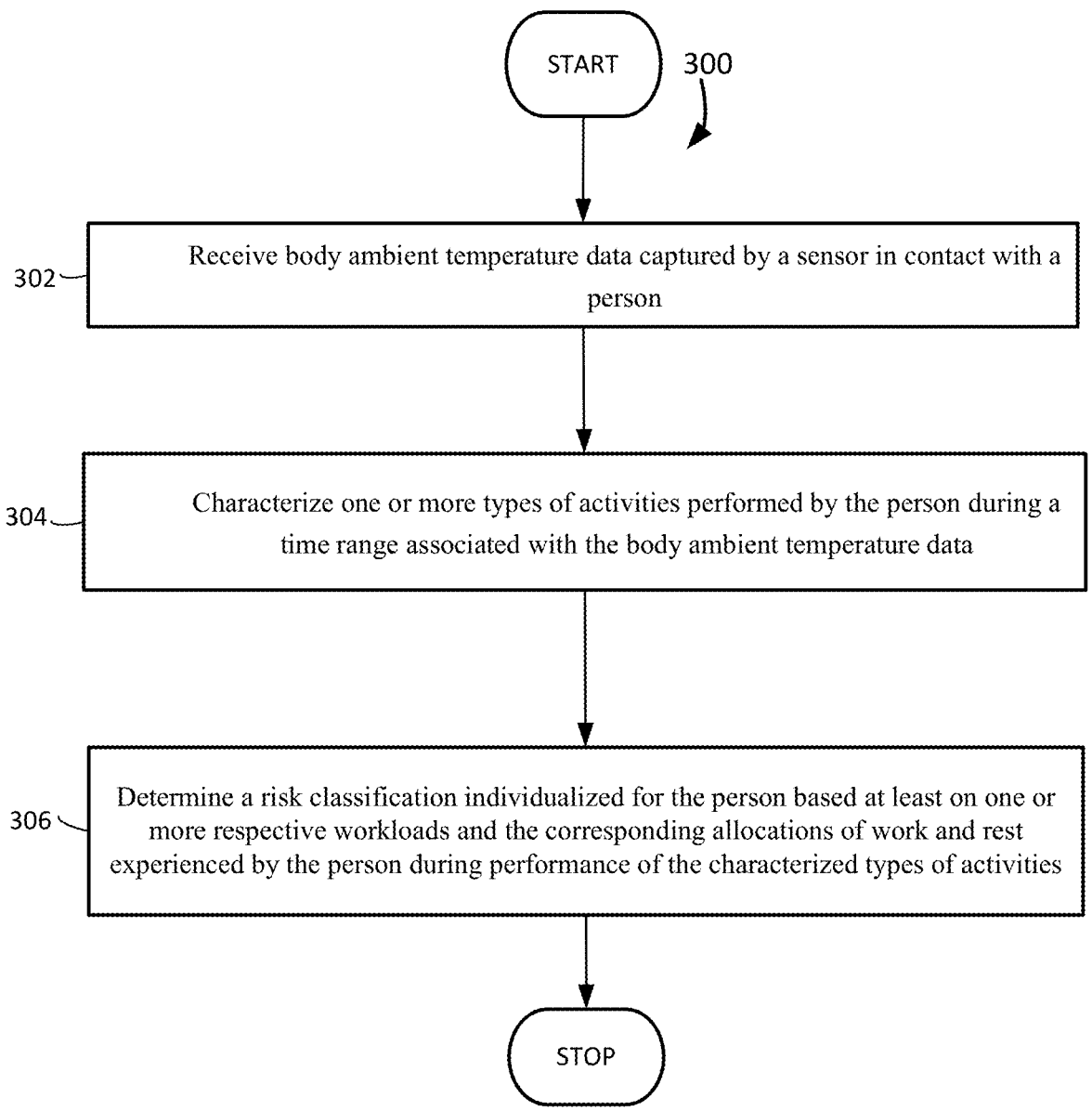
FIG. 3 is an operational flow diagram illustrating a high-level overview of a method for determining a risk assessment, in an embodiment.

As shown in FIG. 3, an operational flow diagram 300 includes step 302 at which the Risk Assessment Engine 106 receiving body ambient temperature data captured by a sensor in contact with a person. For example, the body ambient temperature data may be timestamped data that represents body segment motion, body temperature, heart rate, galvanic skin response (GSR), electromyograms (EMG) and environmental conditions data, such as humidity, pressure and positional information associated with a global navigation satellite system.

At step 304, the Risk Assessment Engine 106 characterizes one or more types of activities performed by the person during a time range associated with the body ambient temperature data. The Risk Assessment Engine 106 identifies external data related to a geographic location of the person. The Risk Assessment Engine 106 trims the start and end of the raw captured body ambient temperature data to result in trimmed body ambient temperature data that encompasses a time period that is relevant to risk assessment, such as the work shift of the person. The Risk Assessment Engine 106 synchronizes the trimmed body ambient temperature data with external data. Synchronization converts the multiple, parallel, asynchronously timestamped raw sensor data in the trimmed body ambient temperature data to fully synchronous data using various interpolation techniques.

The Risk Assessment Engine 106 employs a transformation process to the synchronized data in order to reduce errors and increase data accuracy. For example, there may be multiple transformation modules associated with the Risk Assessment Engine 106, where each module operates in parallel and independently from other transformation modules. Various exemplary transformation modules may be based on methods and techniques similar to those described in U.S. Pat. No. 6,820,025 ("Method and apparatus for motion tracking of an articulated rigid body"). Various exemplary transformation modules may increase the accuracy of three-dimensional positional information by combining global navigation satellite system data, accelerometer data, local ambient pressure data and altitude data from external data sources. Various exemplary transformation modules may also convert sensor motion data to determine the person's caloric consumption.

Once the data is transformed, the Risk Assessment Engine 106 employs an activity characterization process. Activity characterization takes as input the transformed data and performs one or more pattern recognition techniques on the transformed data in order to categorize the transformed data according to similar pre-defined activities. The pattern recognition techniques detect a portion(s) of the transformed data that is indicative of data characteristics expected to be observed during performance of a pre-defined activity, such as sitting, climbing stairs or carrying an object. The Risk Assessment Engine 106 further defines start and end times for each characterized pre-defined activity detected in the transformed data.

At step 306, the Risk Assessment Engine 106 determines a risk classification individualized for the person based at least on one or more respective workloads and the corresponding allocations of work and rest experienced by the person during performance of the characterized types of activities. For example, risk classification by the Risk Assessment Engine 106 may be automated and scale thermal risk analysis of guidelines published by the American Conference of Governmental Hygienists (ACGIH) through digitization of input parameters. The input parameters may be climatization, workloads, allocation of work and wet bulb globe temperature (Wbgt). According to the ACGIH, for a given climatization, workload and work duty cycle, if the measured Wbgt exceeds a specified numerical value then a risk of thermal exposure is present. For example, the ACGIH standards indicate that a climatized individual performing a job with a 60% allocation of work with a heavy workload, must not exceed a Wbgt of 27.5 degrees Celsius to remain safe and not be thermally at risk.

According to various embodiments, new employees or mature employees (such as employees over 55 years of age) working in a constantly changing environment will be classified as "unacclimatized." The "unacclimatized" classification can automatically be determined by the tracking of an employee's daily average Wbgt exposure over the prior 2 weeks on a daily basis. Large changes measured in the daily average Wbgt will classify the climatization to be unacclimatized. Conversely, consistent Wbgt will classify the employee to be acclimatized. Alternatively, the classification could be manually chosen by a properly trained individual should historical data not be present.

Workload is defined for the Risk Assessment Engine 106 by a metabolic rate (MR) in units of watts experienced during performance of tasks and activities that correspond to various workload categories. The metabolic rate can be further refined on an individualized level according to the particular person's measured body weight. The workload can be automatically be determined by having one or more motion sensors worn on the body of the person. Motion data from the motion sensors further allow for the recreation by the Risk Assessment Engine 106 of the person's physical motions that occurred during performance of various tasks and activities. Such recreation of physical motions enables the Risk Assessment Engine 106 to determine a proper characterization of the person's tasks and activities. Therefore, with proper activity characterization in relation to pre-defined activities and knowledge of the person's weight, a metabolic rate estimate and workload category can be established for any given moment in time. In some embodiments, the metabolic rate estimation may be further enhanced with the addition of a heart rate monitor.

Allocation of work for the Risk Assessment Engine 106 is derived according to a historical sliding window of one hour, during which a percentage of time spent at rest vs. not at rest (i.e. light, medium/moderate, heavy, very heavy) is calculated. Risk Classification is a means of representing the degree of thermal risk exposure. Four classifications levels are defined to represent an increasing degree of risk of exposure. In some embodiments, the Risk Assessment Engine 106 re-assessed thermal risk periodically (e.g. every 30 seconds) so that the changes in thermal risk exposure are promptly detected.

Figure 4:
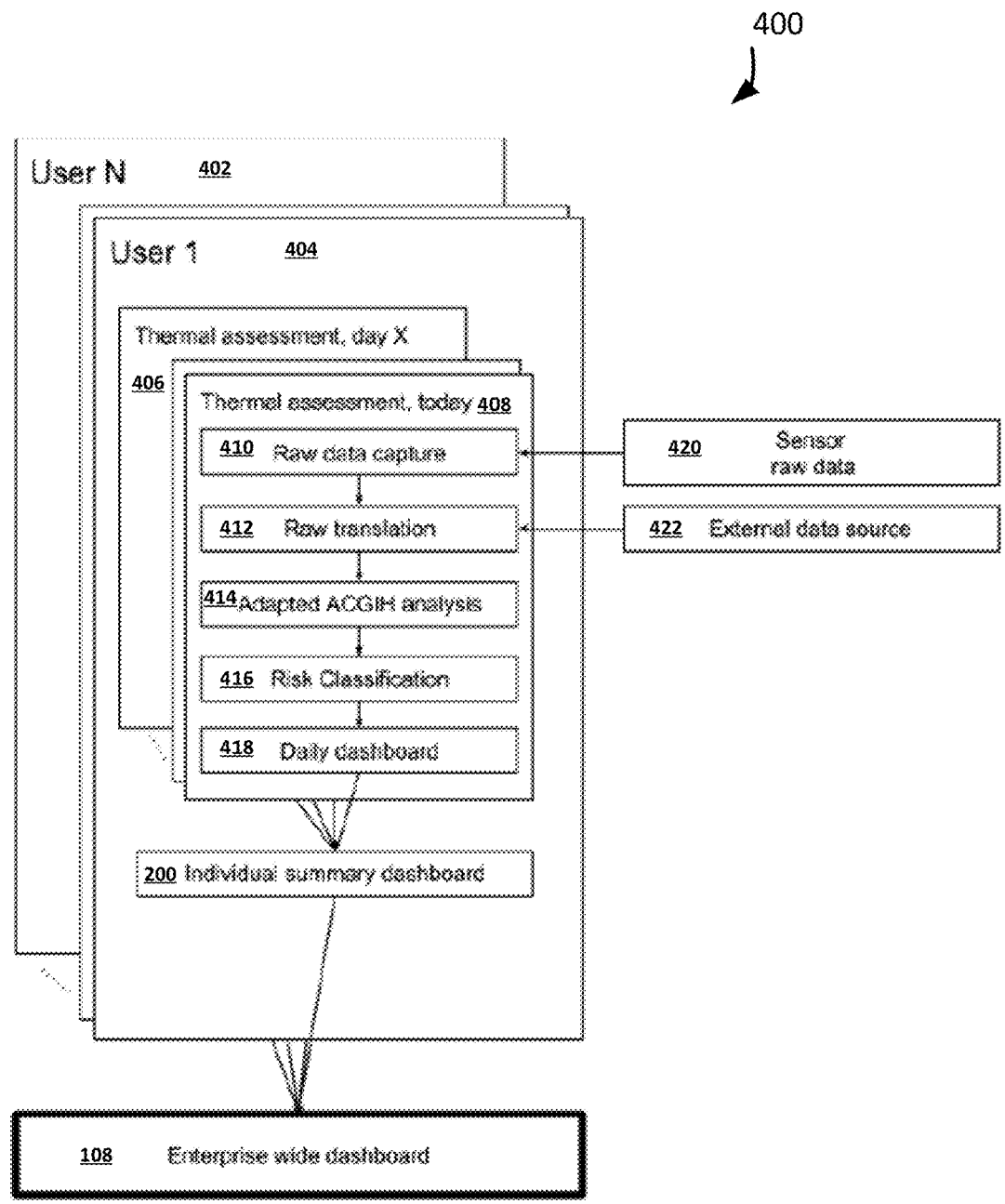
FIG. 4 is a high-level diagram of an exemplary data flow for determining a risk assessment, in an embodiment.

As shown in FIG. 4, the Risk Assessment Engine 106 utilizes a data flow 400 on an individual level and may further refine the data flow to be applied for a various day. For example, the Risk Assessment Engine 106 may separately utilize the data flow 400 with respect to a first employee ("User N") 402 and a second employee ("User 1") 404. The Risk Assessment Engine 106 further refines the data flow 400 for the second employee 404 separately for distinct days 406, 408 (or for distinct work shifts that occurred on different days).

To determine a thermal risk assessment for an employee 404 on a particular day 408, the data flow 400 includes receipt 410 of raw data 420 captured from one or more sensors worn by the employee 404. The raw data 420 may include body segment motion data, body temperature data, heart rate data, galvanic skin response (GSR) data, electromyograms (EMG) data and environmental conditions data comprising at least one of: humidity, pressure and positional information associated with a global navigation satellite system. In response to receipt 410 of the raw data 420, the data flow 400 identifies external data from an external data source(s) 422 with external data related to a geographic location of the employee 404.

The data flow 400 includes raw translation 412 in which transformed data is generated. The transformed data is based on body ambient temperature data from the received raw data 420 that has been synchronized with the external data to represent risk conditions associated with one or more activities performed by the employee 404. To generate the transformed data, the data flow 400 includes trimming the body ambient temperature data and the external data to identify data contemporaneous to timestamps of the raw data 420. The data flow 400 includes generating synchronized data based on synchronizing the trimmed external data and the trimmed body ambient temperature data.

The data flow 400 further includes transforming the synchronized data. For example, physical orientation data of the body ambient temperature data may be transformed to represent one or more body motions. Positional information of the body ambient temperature data may be combined with at least one of: accelerometer data, local ambient pressure from the external data, altitude data from the external data and motion data from the body ambient temperature data in order to generate data representing a relationship between physical energy burn and caloric consumption of the employee 404.

The data flow 400 includes adapted ACGIH analysis 414 during which one or more types of activities performed by the employee 404 are characterized. The data flow includes providing input transformed data to one or more pattern recognition techniques to transformed data. The one or more pattern recognition techniques match at least one or more segments of time associated with the transformed data that is indicative of a time epoch of a performed pre-defined activity available from a plurality of pre-defined activities. The plurality of pre-defined activities comprises, for example: lifting an object, pushing an object, pulling an object, carrying an object, walking, running, standing, sitting, sitting in a moving vehicle and climbing stairs. It is understood that embodiments of the Risk Assessment are not limited to ACGIH standards.

The data flow 400 further includes risk classification 416. Risk classification 416 includes identifying respective workloads of the employee 404 associated with the one or more types of characterized activities performed by the employee 404. According to various embodiments, each respective workload may be based on an established metabolic rate experienced during a pre-defined activity that matches a respective activity represented in part by the body ambient temperature data. A respective allocation of work and rest describes a ratio of rest and non-rest during an interval of time in which a particular type of workload was experienced by the employee 404.

The data flow 400 also includes providing data for display via an individual summary dashboard, such as dashboard 200 described above with respect to FIG. 2.

System Overview

Figure 5:
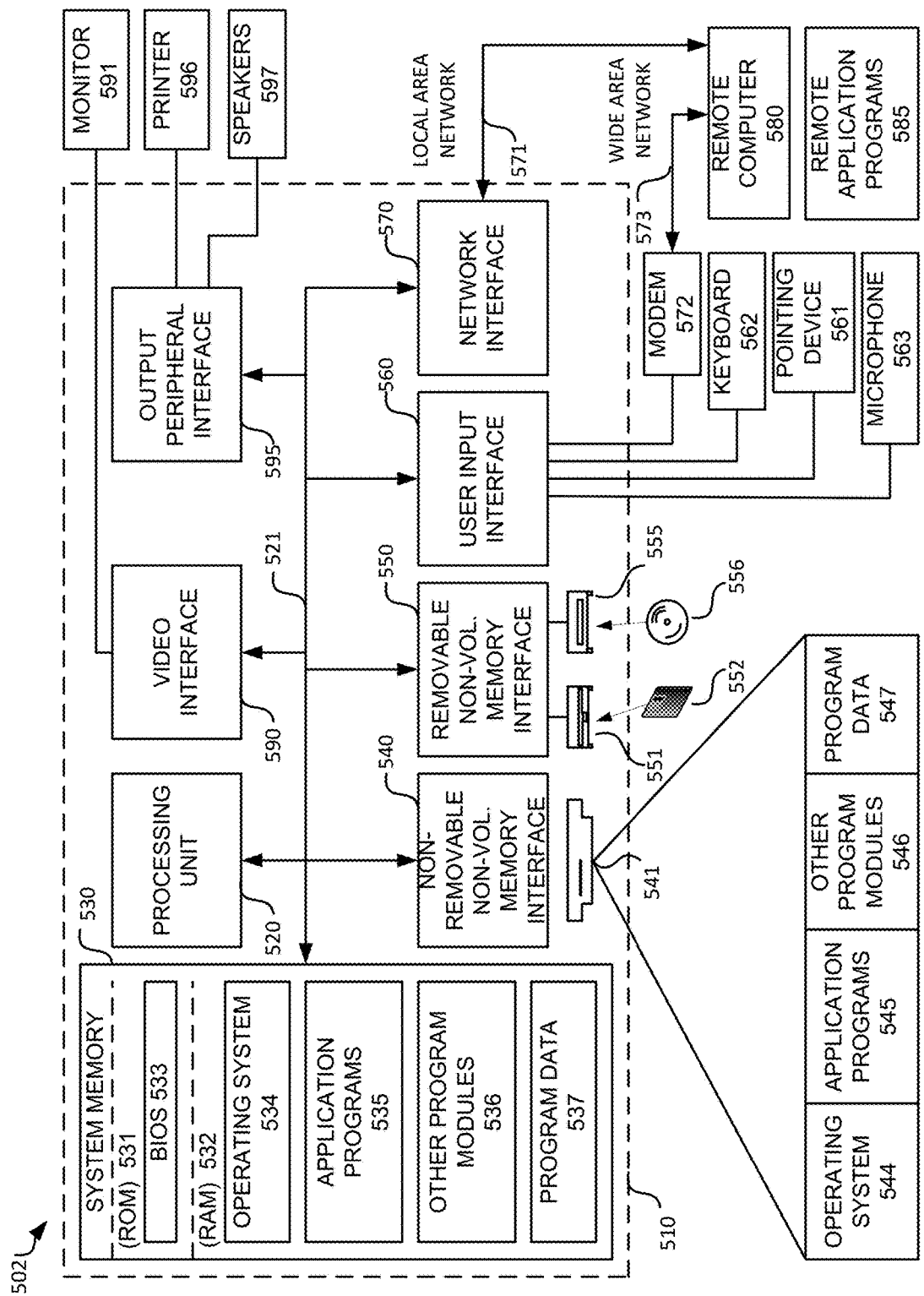
FIG. 5 shows a diagram of an example computing system that may be used with some embodiments.

Referring to FIG. 5, the computing system 502 may include, but are not limited to, a processing unit 520 having one or more processing cores, a system memory 530, and a system bus 521 that couples various system components including the system memory 530 to the processing unit 520. The system bus 521 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) locale bus, and Peripheral Component Interconnect (PCI) bus also known as Mezzanine bus.

The computing system 502 typically includes a variety of computer program product. Computer program product can be any available media that can be accessed by computing system 502 and includes both volatile and nonvolatile media, removable and non-removable media. By way of example, and not limitation, computer program product may store information such as computer readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 502. Communication media typically embodies computer readable instructions, data structures, or program modules.

The system memory 530 may include computer storage media in the form of volatile and/or nonvolatile memory such as read only memory (ROM) 531 and random access memory (RAM) 532. A basic input/output system (BIOS) 533, containing the basic routines that help to transfer information between elements within computing system 502, such as during start-up, is typically stored in ROM 531. RAM 532 typically contains data and/or program modules that are immediately accessible to and/or presently being operated on by processing unit 520. By way of example, and not limitation, FIG. 5 also illustrates operating system 534, application programs 535, other program modules 536, and program data 537.

The computing system 502 may also include other removable/non-removable volatile/nonvolatile computer storage media. By way of example only, FIG. 5 also illustrates a hard disk drive 541 that reads from or writes to non-removable, nonvolatile magnetic media, a magnetic disk drive 551 that reads from or writes to a removable, nonvolatile magnetic disk 552, and an optical disk drive 555 that reads from or writes to a removable, nonvolatile optical disk 556 such as, for example, a CD ROM or other optical media. Other removable/non-removable, volatile/nonvolatile computer storage media that can be used in the exemplary operating environment include, but are not limited to, USB drives and devices, magnetic tape cassettes, flash memory cards, digital versatile disks, digital video tape, solid state RAM, solid state ROM, and the like. The hard disk drive 541 is typically connected to the system bus 521 through a non-removable memory interface such as interface 540, and magnetic disk drive 551 and optical disk drive 555 are typically connected to the system bus 521 by a removable memory interface, such as interface 550.

The drives and their associated computer storage media discussed above and illustrated in FIG. 5, provide storage of computer readable instructions, data structures, program modules and other data for the computing system 502. In FIG. 5, for example, hard disk drive 541 is illustrated as storing operating system 544, application programs 545, other program modules 546, and program data 547. Note that these components can either be the same as or different from operating system 534, application programs 535, other program modules 536, and program data 537. The operating system 544, the application programs 545, the other program modules 546, and the program data 547 are given different numeric identification here to illustrate that, at a minimum, they are different copies.

A user may enter commands and information into the computing system 502 through input devices such as a keyboard 562, a microphone 563, and a pointing device 561, such as a mouse, trackball or touch pad or touch screen. Other input devices (not shown) may include a joystick, game pad, scanner, or the like. These and other input devices are often connected to the processing unit 520 through a user input interface 560 that is coupled with the system bus 521, but may be connected by other interface and bus structures, such as a parallel port, game port or a universal serial bus (USB). A monitor 591 or other type of display device is also connected to the system bus 521 via an interface, such as a video interface 590. In addition to the monitor, computers may also include other peripheral output devices such as speakers 597 and printer 596, which may be connected through an output peripheral interface 590.

The computing system 502 may operate in a networked environment using logical connections to one or more remote computers, such as a remote computer 580. The remote computer 580 may be a personal computer, a handheld device, a server, a router, a network PC, a peer device or other common network node, and typically includes many or all of the elements described above relative to the computing system 502. The logical connections depicted in FIG. 5 includes a local area network (LAN) 571 and a wide area network (WAN) 573 but may also include other networks. Such networking environments are commonplace in offices, enterprise-wide computer networks, intranets and the Internet.

When used in a LAN networking environment, the computing system 502 may be connected to the LAN 571 through a network interface or adapter 570. When used in a WAN networking environment, the computing system 502 typically includes a modem 572 or other means for establishing communications over the WAN 573, such as the Internet. The modem 572, which may be internal or external, may be connected to the system bus 521 via the user-input interface 560, or other appropriate mechanism. In a networked environment, program modules depicted relative to the computing system 502, or portions thereof, may be stored in a remote memory storage device. By way of example, and not limitation, FIG. 5 illustrates remote application programs 585 as residing on remote computer 580. It will be appreciated that the network connections shown are exemplary and other means of establishing a communications link between the computers may be used.

It should be noted that some embodiments described herein may be carried out on a computing system such as that described with respect to FIG. 5. However, some embodiments may be carried out on a server, a computer devoted to message handling, handheld devices, or on a distributed system in which different portions of the present design may be carried out on different parts of the distributed computing system.

Another device that may be coupled with the system bus 521 is a power supply such as a battery or a Direct Current (DC) power supply) and Alternating Current (AC) adapter circuit. The DC power supply may be a battery, a fuel cell, or similar DC power source needs to be recharged on a periodic basis. The communication module (or modem) 572 may employ a Wireless Application Protocol (WAP) to establish a wireless communication channel. The communication module 572 may implement a wireless networking standard such as Institute of Electrical and Electronics Engineers (IEEE) 802.11 standard, IEEE std. 802.11-1999, published by IEEE in 1999.

Examples of mobile computing systems may be a laptop computer, a tablet computer, a Netbook, a smart phone, a personal digital assistant, or other similar device with on board processing power and wireless communications ability that is powered by a Direct Current (DC) power source that supplies DC voltage to the mobile computing system and that is solely within the mobile computing system and needs to be recharged on a periodic basis, such as a fuel cell or a battery.

Figure 6:
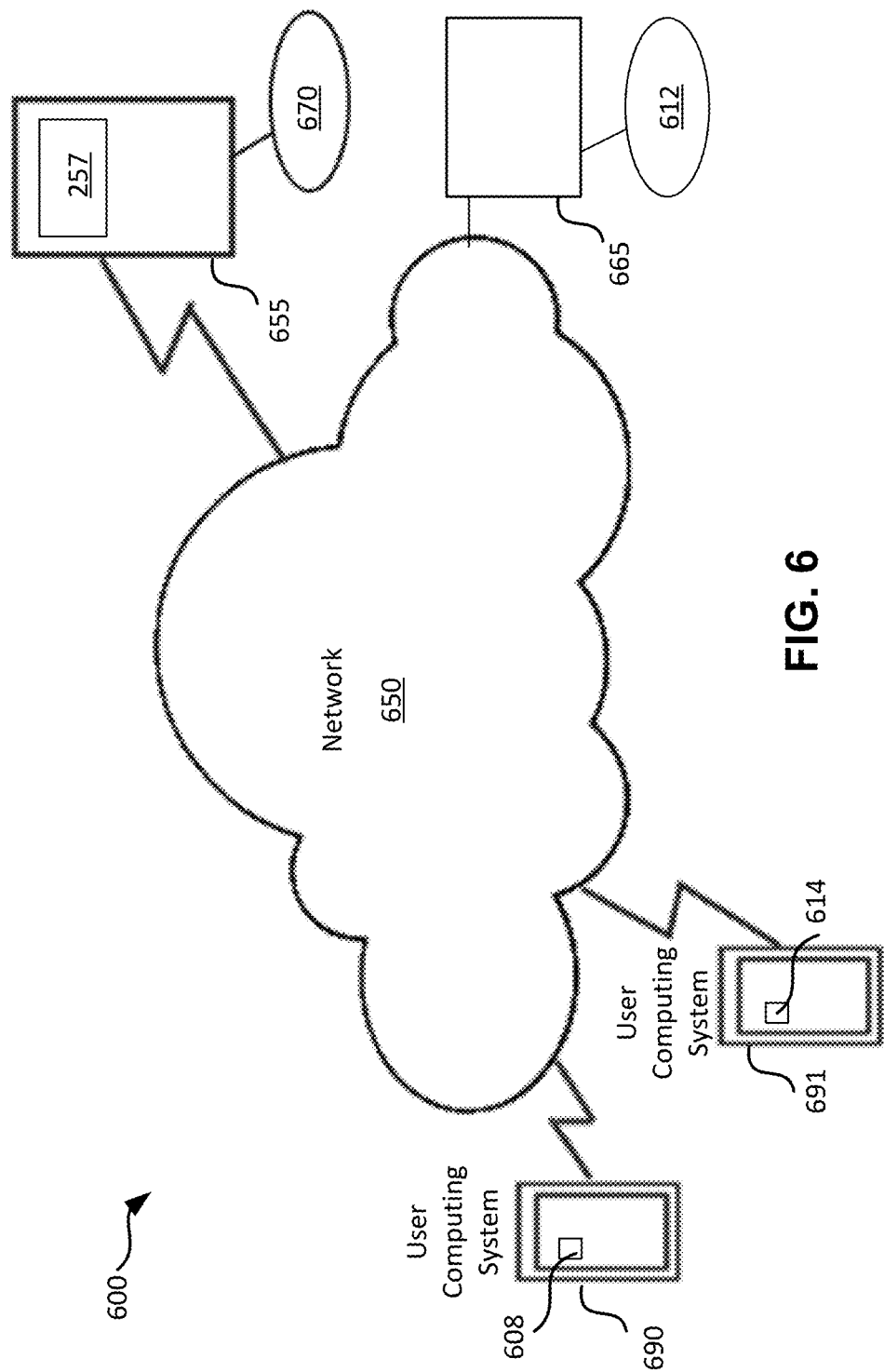
FIG. 6 shows a diagram of an example network environment that may be used with some embodiments.

FIG. 6 shows a diagram of an example network environment that may be used with some of the described embodiments. Network environment 620 includes computing systems 690 and 691. One or more of the computing systems 690 and 691 may be a mobile computing system or a sensor that may be worn on a person's body. The computing systems 690 and 691 may be connected to the network 650 via a cellular connection or via a Wi-Fi router (not shown). The network 650 may be the Internet. The computing systems 690 and 691 may be coupled with server computing systems 655 and 665 via the network 650.

Each of the computing systems 690 and 691 may include an application module such as module 608 or 614. For example, a user (e.g., a developer) may use the computing system 690 and the application module 608 to connect to and communicate with the server computing system 655 and log into application 657.

While one or more implementations have been described by way of example and in terms of the specific embodiments, it is to be understood that one or more implementations are not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

The invention claimed is:

1. A method comprising:
    receiving body ambient temperature data captured by a sensor in contact with a person;
    characterizing one or more types of activities performed by the person during a time range associated with the body ambient temperature data; and
    determining a risk classification individualized for the person based at least on one or more respective workloads and the corresponding allocations of work and rest experienced by the person during performance of the characterized types of activities.

2. The method of claim 1, wherein the body ambient temperature data captured by a sensor comprises time-stamped data representing at least one of:
    body segment motion, body temperature, heart rate, galvanic skin response (GSR), electromyograms (EMG); and
    environmental conditions data comprising at least one of: humidity, pressure and positional information associated with a global navigation satellite system.

3. The method of claim of claim 1, wherein characterizing one or more types of activities comprises:
    identifying external data related to a geographic location of the person; and
    generating transformed data based on the body ambient temperature data synchronized with the external data to represent risk conditions associated with one or more activities performed by the person during the time range of the body ambient temperature data.

4. The method of claim 3, wherein the external data comprises at least one of: weather data and land survey data.

5. The method of claim 3, wherein generating transformed data based on the body ambient temperature data synchronized with the external data comprises:
    trimming the external data to identify trimmed external data contemporaneous to the time range of the body ambient temperature data;
    generating synchronized data based on synchronizing the trimmed external data and the body ambient temperature data; and
    transforming the synchronized data to generate transformed data, the transformed data includes one or more of:
        (i) physical orientation data of the body ambient temperature data transformed to representations of one or more body motions;
        (ii) positional information of the body ambient temperature data combined with at least one of: accelerometer data, local ambient pressure from the external data, altitude data from the external data and motion data from the body ambient temperature data converted into data representing a relationship between physical energy burn and caloric consumption.

6. The method of claim 1, wherein characterizing one or more types of activities performed by the person during a time range associated with the body ambient temperature data comprises:
    applying one or more pattern recognition techniques to transformed data based on external data synchronized with the body ambient temperature data, the one or more pattern recognition techniques matching at least one or more segments of time associated with the transformed data that is indicative of a time epoch of a performed pre-defined activity available from a plurality of pre-defined activities.

7. The method of claim 6, wherein plurality of pre-defined activities comprises: lifting an object, pushing an object, pulling an object, carrying an object, walking, running, standing, sitting, sitting in a moving vehicle and climbing stairs.

8. The method of claim 1, wherein determining a risk classification individualized for the person comprises:
    identifying respective workloads associated with the one or more types of characterized activities and one or more allocations of work and rest when the person incurred each the respective workloads.

9. The method of claim 8, wherein a respective workload is based on an established metabolic rate experienced during a pre-defined activity that matches a respective activity represented in part by the body ambient temperature data; and wherein a respective allocation of work and rest describes a ratio of rest and non-rest during an interval of time in which the respective workload was experienced.

10. A computer program product comprising computer-readable program code to be executed by one or more processors when retrieved from a non-transitory computer-readable medium, the program code including at least one instruction to:

receive body ambient temperature data captured by a sensor in contact with a person;

characterize one or more types of activities performed by the person during a time range associated with the body ambient temperature data; and determine a risk classification individualized for the person based at least on one or more respective workloads and the corresponding allocations of work and rest experienced by the person during performance of the characterized types of activities.

11. The computer program product of claim 10, wherein the body ambient temperature data captured by a sensor comprises timestamped data representing at least one of:

body segment motion, body temperature, heart rate, galvanic skin response (GSR), electromyograms (EMG); and environmental conditions data comprising at least one of: humidity, pressure and positional information associated with a global navigation satellite system.

12. The computer program product of claim 10, wherein the program code to characterize one or more types of activities further includes instructions to:

identify external data related to a geographic location of the person; and generate transformed data based on the body ambient temperature data synchronized with the external data to represent risk conditions associated with one or more activities performed by the person during the time range of the body ambient temperature data.

13. The computer program product of claim 12, wherein the external data comprises at least one of: weather data and land survey data.

14. The computer program product of claim 12, wherein the program code to generate transformed data further includes instructions to:

trim the external data to identify trimmed external data contemporaneous to the time range of the body ambient temperature data;

generate synchronized data based on synchronizing the trimmed external data and the body ambient temperature data; and transform the synchronized data to generate transformed data, the transformed data includes one or more of:

(i) physical orientation data of the body ambient temperature data transformed to representations of one or more body motions;

(ii) positional information of the body ambient temperature data combined with at least one of: accelerometer data, local ambient pressure from the external data, altitude data from the external data and motion data from the body ambient temperature data converted into data representing a relationship between physical energy burn and caloric consumption.

15. The computer program product of claim 10, wherein the program code to characterize one or more types of activities further includes instructions to:

apply one or more pattern recognition techniques to transformed data based on external data synchronized with the body ambient temperature data, the one or more pattern recognition techniques matching at least one or more segments of time associated with the transformed data that is indicative of a time epoch of a performed pre-defined activity available from a plurality of pre-defined activities.

16. The computer program product of claim 15, wherein plurality of pre-defined activities comprises: lifting an object, pushing an object, pulling an object, carrying an object, walking, running, standing, sitting, sitting in a moving vehicle and climbing stairs.

17. The computer program product of claim 10, wherein the program code to determine a risk classification individualized for the person further includes instructions to:

identify respective workloads associated with the one or more types of characterized activities and one or more allocations of work and rest when the person incurred each the respective workloads.

18. The computer program product of claim 17, wherein a respective workload is based on an established metabolic rate experienced during a pre-defined activity that matches a respective activity represented in part by the body ambient temperature data; and wherein a respective allocation of work and rest describes a ratio of rest and non-rest during an interval of time in which the respective workload was experienced.

19. A system comprising:

one or more processors; and a non-transitory computer readable medium storing a plurality of instructions, which when executed, cause the one or more processors to:

receive body ambient temperature data captured by a sensor in contact with a person;

characterize one or more types of activities performed by the person during a time range associated with the body ambient temperature data; and determine a risk classification individualized for the person based at least on one or more respective workloads and the corresponding allocations of work and rest experienced by the person during performance of the characterized types of activities.

20. The system of claim 19, wherein the plurality of instructions, which when executed, cause the one or more processors to characterize one or more types of activities further includes one or more instructions to:

apply one or more pattern recognition techniques to transformed data based on external data synchronized with the body ambient temperature data, the one or more pattern recognition techniques matching at least one or more segments of time associated with the transformed data that is indicative of a time epoch of a performed pre-defined activity available from a plurality of pre-defined activities; and wherein the plurality of instructions, which when executed, cause the one or more processors to determine a risk classification further includes one or more instructions to:

identify respective workloads associated with the one or more types of characterized activities and one or more allocations of work and rest when the person incurred each the respective workloads, wherein a respective workload is based on an established metabolic rate experienced during a pre-defined activity that matches a respective activity represented in part by the body ambient temperature data and wherein a respective allocation of work and rest describes a ratio of rest and non-rest during an interval of time in which the respective workload was experienced.

\* \* \* \* \*